United States Patent [19]

Torimae et al.

[11] Patent Number: 4,787,897
[45] Date of Patent: Nov. 29, 1988

[54] STRETCHABLE FASTENING TAPE FOR DISPOSABLE DIAPER

[75] Inventors: Yasuhiro Torimae; Heihachiro Kawaguchi, both of Wakayama; Yoshinori Takahashi, Utsunomiya, all of Japan

[73] Assignee: Kao Corporation, Tokyo, Japan

[21] Appl. No.: 55,360

[22] Filed: May 29, 1987

[30] Foreign Application Priority Data

Jun. 3, 1986 [JP] Japan .................................. 61-128710

[51] Int. Cl.⁴ .............................................. A61F 13/16
[52] U.S. Cl. .................................. 604/389; 428/343; 428/355; 428/913
[58] Field of Search ....................... 428/343, 355, 913; 604/385.2, 389, 391

[56] References Cited

U.S. PATENT DOCUMENTS

| | | | |
|---|---|---|---|
| 3,920,018 | 11/1975 | Schaar | 604/390 |
| 4,024,312 | 5/1977 | Korpman | 428/343 |
| 4,379,806 | 4/1983 | Korpman | 428/354 |
| 4,460,364 | 7/1984 | Chen et al. | 604/389 X |
| 4,554,191 | 11/1985 | Korpman | 604/389 X |
| 4,643,729 | 2/1987 | Laplanche | 604/389 |
| 4,652,491 | 3/1987 | Gobran | 428/355 |
| 4,704,110 | 11/1987 | Raykovitz et al. | 604/389 X |

Primary Examiner—James J. Bell
Attorney, Agent, or Firm—Birch, Stewart, Kolasch & Birch

[57] ABSTRACT

A stretchable, fastening tape of the invention comprising a solid middle portion made of an elastic material and two solid end portions made of a non-elastic material which are integrally bonded through respective solid boundary regions to said solid middle portion, said end and middle portions having substantially the same structural dimension, and wherein said elastic material being, a composition comprising (a) and (b), or (a), (b) and (c) as defined below, and said non-elastic material is constituted of (d) as defined:

(a) 100 parts by weight of a hydrogenated block copolymer represented by a general formula, A-(B-A)$_n$, wherein A is a block polymer of a monovinyl-substituted aromatic hydrocarbon, B is an elastomeric block polymer of a conjugated diene, the weight ratio of A to B being 20/80 to 40/60, and n is an integer of 1 to 4;

(b) 10 to 80 parts by weight of a resin having a melting or softening point of 80° C. or higher and an average molecular weight of 400 to 2,000;

(c) 0 to 50 parts by weight of a thermoplastic olefin resin; and (d) a resin selected from the group consisting of polyethylene, polypropylene, poly(ethylene-propylene), poly(ethylene-vinyl acetate), and poly(styrene-butadiene), used alone or as a composite resin thereof.

12 Claims, 1 Drawing Sheet

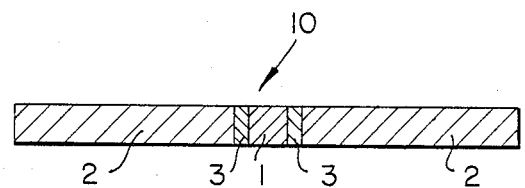
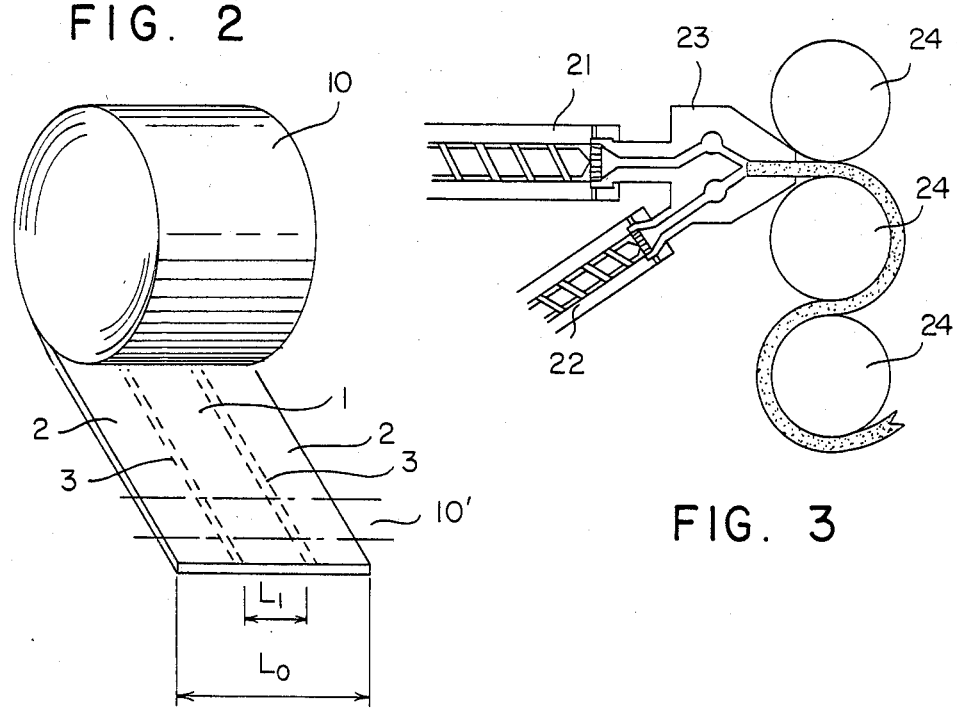
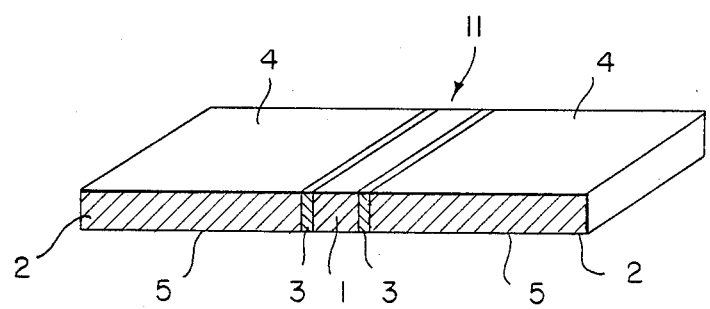

STRETCHABLE FASTENING TAPE FOR DISPOSABLE DIAPER

The present invention relates to a base material for a stretchable fastener tape. More specifically, it relates to a base material for a stretchable fastener tape, which shows excellent flexibility and stretchability, an adequate shrinkage pressure in its use, a small permanent strain, an excellent creep strength, and a good melt-processability, and which is effective for articles worn on human body and involving movement, such as hygienic articles including disposable diapers, clothing, and medical supplies.

Statement of Prior Arts

Conventional fastener tapes generally comprise a base tape material selected from among paper, film, non-woven fabric and cloth, used alone or as composites thereof; and a fastening means, a pressure-sensitive adhesive, or the like applied to the base tape material. They have no stretchability.

Examples of proposed stretchable tapes include a tape for a disposable diaper which comprises an elastic ring or an elastic belt provided in the middle of the tape as disclosed in Japanese Patent Laid-Open No. 68,345/1976 and Japanese Utility Model Laid-Open No. 157,209/1982, and a waist band for a disposable diaper which comprises a low-rigidity base material and a high-rigidity base material as disclosed in Japanese Patent Laid-Open No. 119,944/1985.

A wholly stretchable pressure-sensitive adhesive tape and a thermoplastic stretchable tape are also proposed in Japanese Patent Laid-Open Nos. 235/1978 and 155,478/1984, respectively.

However, problems are involved in using the proposed stretchable tapes as a fastener tape for fixing, for example, an article worn on a human body and involving movement in end use applications wherein stretchability is required or desired. Thus, they are not put into practical use yet.

Specifically, in the case of the fastener tape as disclosed in Japanese Patent Laid-Open No. 68,345/1976, since the elastic material in the middle of the tape has a ring form, elongation of the elastic ring while pinching a tape end portion constituted of a non-elastic material in fixation to an adhered surface for use thereof is liable to cause rupture of the non-elastic material, or deformation attributed to stress concentration in boundary portions between the elastic ring and the non-elastic materials, leading to a marked reduction in the fixation area of a surface of the non-elastic material, in which surface the non-elastic material is fixed to the adherent surface, and hence a decrease in the adhesion. In order to prevent the above-mentioned rupture of the non-elastic material or the above-mentioned deformation, a rigid base material is required as the non-elastic material. In other words, the above-mentioned fastener tape is not suitable as one for an article worn on a human body. Also in an aspect of productivity, the step of connecting the elastic ring with the non-elastic material is complicated, resulting in an economical disadvantage.

On the other hand, a tape structure comprising a belt-like elastic material and non-elastic materials laminated on the back surfaces of both end portions is proposed in Japanese Utility Model Laid-Open No. 157,209/1982. In the above-mentioned structure, however, not only is the productivity notably decreased because a portion where the elastic material is lamination-bonded to the non-elastic material is curled due to a difference in shrinkage factor between the elastic material and the non-elastic material in the forming process or a difference in expansion or shrinkage caused by a change in temperature between storage and use, but also disadvantageously no sufficient bonding surface and hence no sufficient adhesion can be secured unless the whole fixation surface is pressed in every nook and corner in application, while the tape is liable to be peeled from the adherent suface after application due to a curl-reversing force. Further, the tape forming processability is notably damaged due to a difference in thickness between the portion constituted of only the elastic material and the portion where the non-elastic material is laminated thereon. Furthermore, since the elastic material extends to the portion where it is essentially unnecessary, economical disadvantages are caused by not only the elastic material itself but also the lamination step in an aspect of productivity in addition to the above-mentioned disadvantage.

Japanese Utility Model Laid-Open No. 157,209/1982 includes an abstract description about a possibility of a stretchable tape having no difference in thickness between the elastic portion and the non-elastic portion but no disclosure of specific techniques.

As for the waist band for a disposable diaper as disclosed in Japanese Patent Laid-Open No. 119,944/1985, it is mentioned that the base material thereof is constituted of a laminate sheet comprising a non-woven fabric and a plastic film, and that the lamination state of a low-rigidity region is provided by partial or overall thermal fusion in order to avoid an increase in rigidity of the base material. The meaning of low rigidity and high rigidity is expressed in terms of L value according to JIS-P 8143-1967. JIS-P 8143-1967 is concerned with the method of testing the stiffness of paper by self-bending, which cannot serve as a measure for evaluating a stretchability exceeding at least 100%. In view of the fact that the base material is constituted of a laminate sheet comprising a non-woven fabric and a plastic sheet, stretchability exceeding at least 100% cannot be expected in the waist band for the disposable diaper as disclosed in this patent literature. When consideration is also given to the object aimed at by the waist band for the disposable diaper as disclosed in the patent literature, this waist band is unsuitable as a fastener tape which must have excellent flexibility and stretchability, an adequate shrinkage pressure in its use, and a small permanent strain.

The adhesive tape as disclosed in Japanese Patent Laid-Open No. 325/1978 which can usually be easily peeled when the tape is elongated in the longitudinal direction for separating the adhesive from the tape-applied surface, comprises a base material made of only a highly stretchable elastomeric film and a pressure-sensitive adhesive layer applied to at least one whole surface of the base material. This tape aims at easy and painless peeling like a first-aid sticking plaster, and hence cannot perform as a fastener tape for an article involving movement. This is because it is of a different nature from the fastener tape of the present invention aiming at fixation of an article involving movement.

The thermoplastic stretchable tape as disclosed in Japanese Patent Laid-Open No. 155,478/1984 aims at providing a stretchable gathering portion as desired. Accordingly, the whole of the tape is constituted of a stretchable composition. Even when a pressure-sensitive adhesive composition is applied to the stretchable tape, no function of fixation for an article involving movement can be secured like the tape as disclosed in Japanese Patent Laid-Open No. 235/1978.

BRIEF DESCRIPTION OF DRAWINGS

FIG. 1 is an enlarged crosssectional view of an example of the base material for the stretchable fastener tape according to the present invention;

FIG. 2 is a perspective view of an example of the base material for the stretchable fastener tape according to the present invention;

FIG. 3 is a schematic diagram showing an example of process for preparing the base material for the stretchable fastener tape according to the present invention; and FIG. 4 is a schematic perspective view of a fastener tape using a base material for a stretchable fastener tape according to the present invention.

1: elastic material portion
2: non-elastic material portion
3: boundary portion
4: surface coated with pressure-sensitive adhesive
5: surface treated with release agent
10: base material for stretchable fastener tape
11: stretchable fastener tape
21: extruder for non-elastic material
22: extruder for elastic material composition
23: die
24: cooling rolls As described above, mainly in the field of disposable diapers, there have been several proposals concerning a means for materializing usefulness of a stretchable fastener tape having an elastic material provided in the middle portion thereof. However, every proposal involves various problems yet to be solved before it is put into practical use.

The present invention has been made as a result of intensive investigations with a view to solving the above-mentioned problems and providing a fastener tape showing excellent flexibility and stretchability, an adequate shrinkage pressure in its use, a small permanent strain, an excellent creep strength, and good melt processability. The objects of the present invention have been attained by a combination of an elastic material made of a specific composition and a specific nonelastic material bonded to each other according to a specific method.

Specifically, in accordance with the present invention, there is provided a base material for a stretchable fastener tape comprising a middle portion made of an elastic material and two end portions made of a nonelastic material and integrally bonded through respective boundary regions to said middle portion, characterized in that said elastic material is constituted of a composition comprising (a) and (b), or (a), (b) and (c) as mentioned below, while said non-elastic material is constituted of (d) as mentioned below:

(a) 100 parts by weight of a hydrogenated block copolymer represented by a general formula, A-(B-A)$_n$, wherein A is a polymer block of a monovinyl-substituted aromatic hydrocarbon, B is an elastomeric polymer block of a conjugated diene, the weight ratio of A to B is 20/80 to 40/60, and n is an integer of 1 to 4;

(b) 10 to 80 parts by weight of a resin having a melting or softening point of 80° C. or higher and an average molecular weight of 400 to 2,000;

(c) 0 to 50 parts by weight of a thermoplastic olefin resin; and (d) a resin selected from the group consisting of polyethylene, polypropylene, poly(ethylene-propylene), poly(ethylene-vinyl acetate), and poly(styrene-butadiene), used alone or as a composite resin thereof.

The term "excellent flexibility and stretchability" as mentioned in the present invention means an elongation at breakage of an elastic portion of 300% or more and a tenacity at 200% elongation of 3.0 kg or lower per width of a fastener tape formed. The term "adequate shrinkage pressure in its use" means hysteresis loss of 10 to 70% in an S-S hysteresis curve at 200% elongation of an elastic portion. The term "small permanent strain" means a residual strain of 40% or smaller as measured one minute after an elastic portion is elongated by 150% and kept in an elongated state for 3 hours, followed by removal of the load. The term "excellent creep strength" means a creep strength at 40° C. under a load of 1.5 kg of an elastic material of 2 hours or longer per width of a fastener tape formed. The term "good melt-processability" means a capacity of economically and continuously forming a multi-row compositive sheet composed of an elastic material and a non-elastic material and having a thickness of 100 to 350μ from respective compositive without any substantially uneven thickness and any substantially nonuniform appearance according to the melt-coextrusion method while providing a very high adhesion in in the bonding interface between the elastic material and the non-elastic material of the formed multi-row composite sheet.

There are combinations against a desirable tendency among these physical properties themselves and between them and melt-processability. In the prior art technique, for example, the creep strength lowers when improvements in the flexibility and stretchability are aimed at, while the flexibility and stretchability lowers with an increase in permanent strain and a reduction in melt-processability when an improvement in the creep strength is aimed at. When an improvement in the permanent strain is aimed at, the shrinkage pressure increases too much. When an improvement in the melt-processability is aimed at, the creep strength extremely lowers. Accordingly, a specific composition and a specific processing method are necessary in order to satisfy all these contradictory properties.

The component (a) constituting the elastic portion in the present invention is a hydrogenated block copolymer represented by a general formula: A-(B-A). In the above general formula, A is a polymer block of a monovinyl-substituted aromatic hydrocarbon, B is an elastomeric polymer block of a conjugated diene, and n is an integer of 1 to 4. There is no limitation as to the method of preparing such a hydrogenated derivative. In order to secure a necessary creep strength while maintaining the melt-processability and the physical properties on favorable levels, the hydrogenated derivative must have 80 or more of the conjugated diene block of the above general formula hydrogenated.

The monovinyl-substituted aromatic hydrocarbon as the monomer constituting the block A of the copolymer is preferably styrene. α-Methylstyrene or the like may also be used. Preferred conjugated monomers in the block B of the copolymer are butadiene and isoprene. A mixture of the two monomers may also be used. The weight ratio of the block A to the block B of the copolymer is 20/80 to 40/60. When this ratio is less than 20/80, the creep strength is inferior while the sheet surface is sticky. When the weight ratio is more than 40/60, the sheet is too rigid. The number-average molecular weight of the whole copolymer according to GPC is 20,000 or more, preferably 30,000 to 250,000, still preferably 40,000 to 200,000. Too low or high a molecular weight provides poor melt-coextrusion processability of the resulting elastic composition. Examples of preferred hydrogenated derivatives include Kraton G-1650 and Kraton G-1652 manufactured by Shell Chemical Company. They may be used alone or in mixture.

The component (b) to be used in the present invention is a resin having a melting or softening point of 80° C. or higher, preferably 100° C. or higher, particularly preferably 120° C. or higher, and a molecular weight of 400 to 2,000, preferably 600 to 1,500. Specific examples of such a resin include hydrogenated terpene resins and alicyclic hydrocarbon resins. When the melting or softening point is lower than 80° C., the creep strength is lowered. The blending amount of the component (b) is 10 to 80 parts by weight, preferably 20 to 40 parts by weight, per 100 parts by weight of the component (a). When it is less than 10 parts by weight, the melt-coextrusion processability is poor. When it exceeds 80 parts by weight, the creep strength is lowered while the sheet surface is sticky, thus resulting in poor processability.

The component (b) to be used in the present invention is indispensable for the purpose of satisfying both of creep strength and melt-coextrusion processability of a thin sheet having excellent flexibility and stretchability. In the case of rubber as a general elastomer, a mineral oil softener of naphthene, paraffin, aroma or the like type called process oil or extender oil is used for the purpose of improving the softening power and processability. Since the component (a) of the present invention is a thermoplastic elastomer not cross-linked while the desired sheet is thin, a general combination with a softener may be able to improve the processability but notably decreases the creep strength. The component (b) characteristically performs as a processing aid in melt-coextrusion at a high temperature of 170° to 240° C., while the creep strength thereof does not decrease at the service temperatures of the formed product, namely 10° to 40° C. Accordingly, a common softener can be secondarily used together with the component (b) within a range where the creep strength is not lowered.

The component (c) to be used in the present invention contributes to an adequate shrinkage pressure and, in other words, an adequate hysteresis loss as well as an improvement in creep strength. The blending amount of the component (c) can be chosen within a range of 50 parts by weight or less per 100 parts by weight of the component (a) in accordance with specific levels of hysteresis loss and creep strength desired in specific end use application. When the blending amount of the component (c) exceeds 50 parts by weight, the flexibility and stretchability are notably decreased with a notable increase in permanent strain. When it is up to 25 parts by weight, the increase in permanent strain is slow while an increase in hysteresis loss and an improvement in creep strength can be attained. When it is between 25 and 50 parts by weight, an increase in hysteresis loss, an improvement in creep strength, and an increase in permanent strain are observed. In the use of the resulting product as, for example, a fastener tape of a disposable diaper, the preferred blending amount is 20 to 30 parts by weight. Preferred resins include a low-density polyethylene having a density of 0.917 to 0.935 or its modified products. Particularly preferred resins include a low-density polyethylene having a M.F.R. (ASTM D 1238) value of 0.25 to 2.5 and its modified products.

Needless to say, a pigment, a filler, a stabilizer, etc., which are usually used for a thermoplastic polymer, may be added to a composition of the elastic material if desired.

The component (d) to be used in the non-elastic material in the present invention is a thermoplastic resin selected from among polyethylene, polypropylene, poly(ethylene-propylene), poly(ethylenevinyl acetate), and poly(styrene-butadiene) and having an Olsen rigidity (ASTM D 747) of 600 to 15,000, preferably 900 to 6,000, used alone or as a composite resin thereof, which has a stress in 10% elongation of twice or more, preferably 5 times or more, that of the elastomer to be combined therewith.

The non-elastic material portion of a fastener tape has a fastening agent layer provided on one surface thereof, which layer serves to fix articles to each other. Although a higher rigidity is desired from the viewpoint of easiness in application of the tape, a lower rigidity and a higher softness are preferred for giving a soft touch. The flowability and adhesion of the component (d) in a molten state thereof must have some approximation to those of the elastic material composition from the viewpoint of melt-coextrusion processability of the component (d) with the elastic material composition. The composition (d) was chosen as the one satisfying these three requirements. Needless to say, a pigment, a filler, a stabilizer, etc., which are usually used for a thermoplastic polymer, may be added if desired.

The most desirable method of forming a multi-row composite sheet having an elastic material and a non-elastic material integrally bonded to each other in end portions thereof enough boundary regions is a melt-coextrusion method. Two extruders respectively feed a thermoplastic elastic material composition and a non-elastic material composition into one die. The compositions are delivered from a die lip and cooled with cooling rolls to form a multi-row composite sheet having an elastic material portion and a non-elastic material portion alternately aligned, namely a base material for a stretchable fastener tape according to the present invention. The forming temperature is preferably 170° to 240° C. The shear rate of the molten resins in the die lip is $5 \times 10^1$ to $9 \times 10^2$ for both of the elastic material and the non-elastic material.

A fastening agent layer is provided on at least one surface of the non-elastic material of the obtained multi-row composite sheet as the base material according to a customary method, and if desired, the back surface is treated with a release agent, followed by slitting to a desired width. Thus, a fastener tape is obtained. Although the fastening agent layer should be basically provided on the surface of the non-elastic material in order for the fastener tape to manifest the above-mentioned various performances, there may be an overcoated fastening agent layer extending on the surface of the elastic material portion in so far as the stretchability of the elastic material portion is not obstructed.

The base material for the fastener tape according to the present invention is effective in fixing an article worn on a human body and involving movement and especially effective in fixing a disposable diaper. When the base material for the fastener tape according to the present invention is used in fixing a disposable diaper, it is desired to satisfy the following conditions (a) to (c):

(a) the thickness of the base material for the fastener tape is 100 to 350μ;

(b) the tenacity in 200% elongation of the elastic material is 3.0 kg or lower per width of the fastener tape formed; and (c) the ratio ($L_1/L_0$) of the length $L_1$ in the longer direction of the elastic material to the total length $L_0$ of the fastener tape is 0.05 to 0.25.

[EXAMPLE]

The following Examples will now more specifically illustrate the stretchable fastener tape according to the present invention.

Examples 1 to 8 as against Comparative Examples 1 to 5 show embodiments of the elastic material portion which plays an important role in the present invention, while Examples 9 to 13 as against Comparative Examples 6 and 7 show embodiments of the base material for the fastener tape which uses an elastic composition having favorable properties.

EXAMPLES 1 TO 8 AND COMPARATIVE EXAMPLES 1 TO 5

Components as listed in Tables 1 and 2 were kneaded with 8-inch rolls, followed by pulverization. A sheet made of only an elastic material and having a thickness of 300μ was formed with a Labo Plastomill (manufactured by Toyo Seiki K.K.), followed by measurement of its physical properties.

The results are shown in Tables 1 and 2. The values of physical properties are ones measured per 25 mm in width.

EXAMPLES 9 TO 13 AND COMPARATIVE EXAMPLES 6 AND 7

A composition listed as the elastic material composition in Table 3 and another composition also listed as the non-elastic material composition in Table 3 were fed in a thermally plasticized state thereof from extruders 22 and 21, respectively, to a die 23, which was a coextrusion die having a structure capable of coalescing therein a molten elastic material composition and a molten non-elastic material composition which structure has a die lip width of 125 mm and a clearance of 1 mm, and allows a middle elastic material portion to be formed to provide a width of 7 mm. An integrated composite body of the molten elastic material composition and the molten non-elastic material composition was fed through the die 23 to cooling rolls 24, followed by slitting both thick end portions formed due to neck-in. Thus, a continuous integrated composite sheet as shown in FIG. 2, which had a structure as shown in FIG. 1 and a total width of 65 mm, was obtained. The forming conditions, and the moldability and properties of the resulting base material for the fastener tape are shown in Tables 4 and 5, respectively.

In Comparative Example 6, an elastic material composition was only intermittently extruded from the die lip, so that integration thereof with a non-elastic material for forming a composite was impossible. It might have been due to insufficient gelation. When the forming temperature was further raised, extrusion became impossible due to the thermal deterioration of unsaturated bonds. Such a situation was expressed by a symbol x in the ranks of "thickness" and "width" of the elastic material portion in Table 5.

In Comparative Example 7, an elastic material composition was extruded in a wavy form from the die lip. Although it was pressed with nip rolls, merely an elastic material having nonuniform thickness and width was obtained.

The ratio ($L_1/L_0$) of the length $L_1$ in the longitudinal direction of the elastic material to the total length $L_0$ of the fastener tape was 0.11. $L_1$ and $L_0$ are shown in FIG. 2.

The elastic material composition was preliminarily mixed with a high velocity mixer for plastics and melt-kneaded with a biaxial extruder to form pellets.

TABLE 1

| | Composition and Physical Properties of Elastic Material Portion | | | | | | | |
|---|---|---|---|---|---|---|---|---|
| Ex. No. | 1 | 2 | 3 | 4 | 5 | 6 | 7 | 8 |
| (a) Kraton G-1652*[1] | 100 | 100 | 100 | 100 | 100 | 100 | 100 | 100 |
| (b) Clearon P105*[2] | 30 | 30 | 50 | 50 | 70 | — | — | — |
| Arkon P100*[3] | — | — | — | — | — | 30 | 50 | 80 |
| (c) L-LDPE*[4] | — | 10 | — | 20 | — | — | — | — |
| Elongation at break, % | 500 | 500 | 530 | 510 | 430 | 500 | 510 | 470 |
| Tenacity at 200% elongation, kg | 1.3 | 2.1 | 1.3 | 2.6 | 2.0 | 1.4 | 1.6 | 1.9 |
| Creep strength, hr | 6 | >10 | 4 | 9 | 3 | 6 | 3 | 2 |

(Note)
*[1]Shell Chemical; hydrogenated derivative of styrene-butadiene copolymer
*[2]Yasuhara Yushi Kogyo; hydrogenated terpene resin, solftening point: 105° C.
*[3]Arakawa Kagaku Kogyo; alicyclic saturated hydrocarbon resin, softening point: 100° C.
*[4]Mitsui Petrochemical Industries, Ltd.; Ultzex 3021F

TABLE 2

| | Composition and Physical Properties of Elastic Material Portion | | | | |
|---|---|---|---|---|---|
| Com. Ex. No. | 1 | 2 | 3 | 4 | 5 |
| Kraton G-1652 | — | — | — | 100 | — |
| Kraton G-1650 | — | — | — | — | 100 |
| Solprene 406*[1] | — | 100 | 100 | — | — |
| AR 460C*[2] | 100 | — | — | — | — |
| Shellflex 371J*[3] | — | — | 30 | 30 | 30 |
| CaCO$_3$*[4] | 25 | — | 30 | — | 25 |
| Elongation at break | 600 | 750 | 830 | 550 | 550 |
| Tenacity at 200% elongation | 1.5 | 2.4 | 1.0 | 2.3 | 1.4 |
| Creep strength | <0.1 | >10 | >10 | <0.1 | 0.4 |

(Note)
*[1]Asahi Chemical Industry Co., Ltd.; styrene-butadiene block copolymer
*[2]Aron Chemical Kogyo; styrene-butadiene block copolymer compound
*[3]Shell Chemical; naphthenic extender oil
*[4]Average particle size: 1μ, surface-treated grade

TABLE 3

Composition of Elastic Material Portion and Non-Elastic Material Portion

| | | | Ex. No. | | | | | Com. Ex. No. | |
|---|---|---|---|---|---|---|---|---|---|
| | | | 9 | 10 | 11 | 12 | 13 | 6 | 7 |
| Elastic material portion | (a) | Kraton G-1652 | 100 | 100 | 100 | 100 | 100 | — | — |
| | | Solprene 406 | — | — | — | — | — | 100 | 100 |
| | (b) | Clearon P-105 | 30 | 30 | 30 | — | — | — | — |
| | | Clearon P-125*1 | — | — | — | 30 | — | — | — |
| | | Arkon P14*3 | — | — | — | — | 30 | — | — |
| | (c) | L-LDPE*2 | — | 20 | 40 | 20 | 20 | — | — |
| | | CaCO3 | 20 | — | — | — | — | — | — |
| | | Shellflex 371JY | — | — | — | — | — | — | 30 |
| Non-elastic material portion | | | F951-4*4 | H616-3*5 | H616-3 | H616-3 | H616-3 | H616-3 | H616-3 |

(Note)
*1Yasuhara Yushi; hydrogenated terpene resin, softening point: 125° C.
*2Mitsui Petrochemical Industries, Ltd.; Ultzex 3021F
*3Arakawa Kagaku Kogyo; alicyclic saturated hydrocarbon resin; softening point: 140° C.
*4Mitsui Petrochemical Industries, Ltd.; Mirason F951-4 (LDPE)
*5Mitsui Petrochemical Industries, Ltd.; Mirason H616-3 (LDPE containing 3.5% of VAc)

TABLE 4

Forming Conditions

| Ex. No. and Com. Ex. No. | Temp. of extruder ($C_1, C_2, C_3$) °C. | | Temp. of die °C. | Amount of extrusion (cc/min) | | Sheet winding rate (m/min) |
|---|---|---|---|---|---|---|
| | Elastic material | Non-elastic material | | Elastic material | Non-elastic material | |
| Ex. 9 | 150,180,190 | 150,190,190 | 190 | 6.1 | 104.1 | 3.5 |
| Ex. 10 | 150,180,190 | 150,190,190 | 190 | 4.9 | 104.1 | 3.5 |
| Ex. 11 | 150,180,190 | 150,190,190 | 190 | 4.9 | 83.3 | 3.5 |
| Ex. 12 | 150,190,190 | 150,190,190 | 190 | 4.9 | 86.3 | 3.5 |
| Ex. 13 | 150,190,190 | 150,190,190 | 190 | 4.9 | 83.3 | 3.5 |
| Com. Ex. 6 | 160,190,200 | 150,190,190 | 200 | 4.9 | 83.3 | 3.5 |
| Com. Ex. 7 | 150,180,190 | 150,190,190 | 190 | 4.9 | 83.3 | 3.5 |

TABLE 5

Moldability and Physical Properties of Base Material for Fastener Tape

| | | Ex. No. | | | | | Com. Ex. No. | |
|---|---|---|---|---|---|---|---|---|
| | | 9 | 10 | 11 | 12 | 13 | 6 | 7 |
| Moldability | | | | | | | | |
| Thickness of elastic material portion, μ | | 250 ± 10 | 200 ± 10 | 200 ± 10 | 200 ± 10 | 200 ± 10 | x | 0~1000 |
| Width of elastic material portion, mm | | 7 ± 0.5 | 7 ± 0.5 | 7 ± 0.5 | 7 ± 0.5 | 7 ± 0.5 | x | 7 ± 4 |
| Thickness of non-elastic material portion, μ | | 250 ± 10 | 250 ± 10 | 200 ± 10 | 200 ± 10 | 200 ± 10 | 200 ± 20 | 200 ± 20 |
| Rating of coextrudability*1 | | o | o | o | o | o | x | x |
| Physical properties per 25 mm in width | | | | | | | | |
| Elastic material portion | Elongation at break, % | 520 | 500 | 480 | 480 | 460 | — | — |
| | Tenacity at 200% elongation, kg | 1.1 | 1.4 | 1.9 | 1.5 | 1.6 | — | — |
| | Hysteresis loss, % | 15 | 20 | 50 | 21 | 25 | — | — |
| | Permanent strain, % | 15 | 15 | 34 | 17 | 20 | — | — |
| | Creep strength, hr | 5 | 8 | >10 | >10 | >10 | — | — |
| Olsen rigidity of non-elastic material portion, kg/cm | | 1600 | 1100 | 1100 | 1000 | 1100 | 1100 | 1100 |
| Bonding of elastic material portion/non-elastic material portion | | o | o | o | o | o | o | o |

(Note)
*1, o; The width of the elastic material portion is within a predetermined width ±1 mm, while its thickness is within a predetermined thickness ±50μ.
x; The width of the elastic material portion is over a predetermined ±1 mm, while its thickness is over a predetermined thickness ±50μ.
*2, o; When the non-elastic material portions in both end portions are pulled to elongate the middle elastic material portion, the non-elastic material portions show irreversible elongation before breakage occurs in the bounding regions thereof.

A block copolymer corresponding to the component (a) in Comparative Examples 1 and 3 in Table 2 is a styrene-butadiene block copolymer. The creep strength in Comparative Example 1 was so extremely low that it was unsuitable from the viewpoint of practical use, while the basic physical properties were favorable in Comparative Examples 2 and 3. As shown in Comparative Examples 6 and 7 in Table 5, however, moldability of a system using this block copolymer was too poor to form a composite sheet capable of being put into practical use even when an extender oil was combined therewith as the processing aid. Although a block copolymer corresponding to the component (a) according to the present invention was used in Comparative Examples 4 and 5 in Table 2, blending of an extender oil therewith for the purpose of improving the processability extremely lowered the creep strength.

On the other hand, the basic physical properties were satisfied in Examples 1 to 8 according to the present invention in Table 1, while the base materials for the fastener tape according to the present invention in Examples 9 to 13 had a sheet thickness of 200 to 250μ, and very good moldability and physical properties.

Fastener tapes as shown in FIG. 4 which were prepared by treating the back surface 5 of the composite base material sheet in Example 10 with a silicone release agent, applying a rubber hot-melt pressure-sensitive adhesive to the surface of the non-elastic material portion 4, and cutting the resulting material to a width of 25 mm and a total length of 65 mm, namely stretchable fastener tapes composed of a middle elastic matrial portion 1 having a length of 7 mm in the longitudinal direction and non-elastic material portions 2 having a length of 29 mm in both ends, were used as ones for a baby disposable diaper for the purpose of making evaluation based on questionnaires. The diapers well followed the movement of a baby with very good fit. Improvements were observed in respect of urine leak and leak due to a loose passage. Further, no break in the fastener tape portion occurred during the use of the diaper. Thus, very good results were obtained.

What is claimed is:

1. A stretchable, fastening tape comprising a middle portion made of an elastic material and two end portions made of a non-elastic material and integrally bonded through respective boundary regions to said middle portion, said end and middle portions having substantially the same structural dimensions and wherein said elastic material is a composition comprising (a) and (b), or (a), (b) and (c) as defined below, and said non-elastic material is (d) as defined below:
   (a) 100 parts by weight of a hydrogenated block copolymer represented by a general formula, A-(B-A)$_n$, wherein A is a block polymer of a monovinyl-substituted aromatic hydrocarbon, B is an elastomeric block polymer of a conjugated diene, the weight ratio of A to B being 20/80 to 40/60, and n is an integer of 1 to 4;
   (b) 10 to 80 parts by weight of a resin having a melting or softening point of 80° C. or higher and an average molecular weight of 400 to 2,000;
   (c) 0 to 50 parts by weight of a thermoplastic olefin resin; and
   (d) a resin selected from the group consisting of polyethylene, polypropylene, poly(ethylene-propylene), poly(ethylene-vinyl acetate), and poly(styrene-butadiene), used along or as a composite resin thereof.

2. The stretchable fastening tape as claimed in claim 1, wherein said boundary regions between said middle portion and said two end portions are formed by melt-extrusion of both or either of a mass of said elastic material and said non-elastic material.

3. The stretchable fastening tape as claimed in claim 1 having a creep strength, wherein said creep strength at 40° C. under a load of 1.5 kg of said elastic material is 2 hours or longer per width of a fastener tape formed.

4. The stretchable fastening tape as claimed in claim 3, which is used to fix an article worn on a human body.

5. The stretchable fastening tape as claimed in claim 3, which is used to fix a disposable diaper.

6. The stretchable fastening tape as claimed in claim 5, wherein:
   (a) the thickness of a base material for a fastener tape is 100 to 350μ;
   (b) the tenacity in 200% elongation of said elastic material is 3.0 kg or lower per width of said fastener tape formed; and
   (c) the ratio ($L_1/L_0$) of the length $L_1$ of said elastic material in the longitudinal direction to the total length $L_0$ of said fastener tape is 0.05 to 0.25.

7. In a disposable diaper having fastening tapes, the improvement comprising a stretchable fastening tape according to claim 1.

8. A disposable diaper having stretchable fastening tapes, said stretchable fastening tapes comprising a stretchable, fastening tape comprising a middle portion made of an elastic material and two end portions made of a non-elastic material and integrally bonded through respective boundary regions to said middle portion, said end and middle portions having substantially the same structural dimension and wherein said elastic material being a composition comprising (a) and (b), or (a), (b) and (c) as defined below, and said non-elastic material being (d) as defined below:
   (a) 100 parts by weight of a hydrogenated block copolymer represented by a general formula, A-(B-A)$_n$, wherein A is a block polymer of a monovinyl-substituted aromatic hydrocarbon, B is an elastomeric block polymer of a conjugated diene, the weight ratio of A to B being 20/80 to 40/60, and n is an integer of 1 to 4;
   (b) 10 to 80 parts by weight of a resin having a melting of softening point of 80° C. or higher and an average molecular weight of 400 to 2,000;
   (c) 0 to 50 parts by weight of a thermoplastic olefin resin; and
   (d) a resin selected from the group consisting of polyethylene, polypropylene, poly(ethylene-propylene), poly(ethylene-vinyl acetate), and poly(styrene-butadiene), used along or as a composite resin thereof.

9. The stretchable fastening tape according to claim 1, wherein said mono-vinyl-substituted aromatic hydrocarbon is styrene.

10. The stretchable fastening tape according to claim 1, wherein said B elastomeric polymer of a conjugated diene is made up of butadiene and isoprene.

11. The stretchable fastening tape according to claim 1, wherein said resin having a melting point or softening point of 80° C. or higher and a molecular weight of 400 to 2,000 is selected from the group consisting of hydrogenated terpene resins and alicyclic hydrocarbon resins.

12. The stretchable fastening tape according to claim 1, wherein said thermoplastic olefin resin is a polyethylene having a density 0.917 to 0.935 or a modified product thereof.

* * * * *